United States Patent
Dragoo et al.

(10) Patent No.: US 6,229,061 B1
(45) Date of Patent: *May 8, 2001

(54) PACKAGE CONTAINING ABSORBENT ARTICLES AND INSERTS

(75) Inventors: Jerry L. Dragoo, Fairfield; Glen R. Lash, Cincinnati, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/080,690

(22) Filed: May 18, 1998

Related U.S. Application Data

(63) Continuation-in-part of application No. 08/797,386, filed on Feb. 7, 1997, now abandoned, which is a continuation of application No. 08/608,986, filed on Feb. 29, 1996, now abandoned, which is a continuation of application No. 08/407,833, filed on Mar. 21, 1995, now abandoned.

(51) Int. Cl.[7] .............................. A61B 17/06; A61F 13/15
(52) U.S. Cl. .................. 604/358; 604/385.14; 206/438; 206/494
(58) Field of Search ..................................... 604/317, 358, 604/395, 378, 397, 385.01, 385.02, 385.06, 385.14; 206/812, 438, 440, 494

(56) References Cited

U.S. PATENT DOCUMENTS

| | | | |
|---|---|---|---|
| 3,183,910 | 5/1965 | Patterson | 128/290 |
| 4,199,068 | 4/1980 | Weitzner | 211/49 |
| 4,425,130 | 1/1984 | DesMarais | 604/389 |
| 4,598,528 | 7/1986 | McFarland et al. | 53/430 |
| 4,808,175 | 2/1989 | Hansen | 604/385.1 |
| 4,934,535 * | 6/1990 | Muckenfuhs et al. | 206/610 |
| 5,050,742 * | 9/1991 | Muckenfuhs | 206/610 |
| 5,054,619 * | 10/1991 | Muckenfuhs | 206/610 |
| 5,147,055 | 9/1992 | Samson et al. | 220/254 |
| 5,158,199 | 10/1992 | Pontius | 220/410 |
| 5,163,558 * | 11/1992 | Palumbo et al. | 206/494 |
| 5,377,837 * | 1/1995 | Roussel | 206/494 |
| 5,405,342 | 4/1995 | Roesler et al. | 604/364 |
| 5,443,161 * | 8/1995 | Jonese | 206/581 |
| 5,542,566 * | 8/1996 | Glaug et al. | 221/48 |
| 5,897,542 | 4/1999 | Lash et al. | 604/378 |
| 5,971,153 * | 10/1999 | Bauer et al. | 206/494 |
| 6,026,957 * | 2/2000 | Bauer et al. | 206/494 |
| 6,079,562 * | 6/2000 | Bauer et al. | 206/494 |

\* cited by examiner

*Primary Examiner*—Dennis Ruhl
*Assistant Examiner*—Paul Shanoski
(74) *Attorney, Agent, or Firm*—Jay A. Krebs; Thomas J. Osborne, Jr.; David M. Weirich

(57) ABSTRACT

The present invention provides a package containing absorbent articles and inserts. The package includes at least one first absorbent article having a predetermined absorbent capacity, and at least one insert. When the insert is joined with the absorbent article, either before being placed in the package or by the caretaker before being placed on the wearer, the insert and the first absorbent article together form a combined absorbent article having an absorbent capacity which is greater than the absorbent capacity of the first absorbent article.

17 Claims, 4 Drawing Sheets

PACKAGE CONTAINING ABSORBENT ARTICLES AND INSERTS

This is a continuation-in-part of application Ser. No. 08/797,386, filed on Feb. 7, 1997, abandoned, which is a continuation of application Ser. No. 08/608,986, filed on Feb. 29, 1996, abandoned, which is a continuation of application Ser. No. 08/407,833, filed on Mar. 21, 1995, abandoned.

FIELD OF THE INVENTION

This invention relates to a package containing absorbent articles for the treatment of incontinent infirmities in humans, and more particularly, to a package containing absorbent articles and inserts.

BACKGROUND OF THE INVENTION

Infants and other incontinent individuals wear absorbent articles such as incontinent pads and diapers to receive and contain urine and other body exudates. Absorbent articles function both to contain discharged materials and to isolate these materials from the body of the wearer and from the wearer's garments and bed clothing. Disposable absorbent articles having many different basic designs are known to the art.

The absorbent capacity of an absorbent article necessary to provide containment of bodily fluids without leaking is quite different between daytime and overnight use. Because wear time is usually longer during overnight use as compared to daytime use, the quantity of bodily fluids discharged during overnight use is typically greater than the quantity of bodily fluids discharged during daytime use. Even though the absorbent capacity requirements are quite different, absorbent articles having one level of absorbent capacity are typically used for both daytime and overnight use. Unfortunately, the absorbent capacity is sometimes insufficient for overnight use and the absorbent article leaks.

One solution to the above problem is to provide the user with an insert which may be combined with an absorbent article, such as a disposable diaper, to increase the level of absorbent capacity. Diaper inserts or liners are shown in a number of U.S. patents. Representative U.S. patents include U.S. Pat. No. 2,141,105 which issued to J. A. Eller et al. on Dec. 20, 1938 and shows an absorbent pad secured inside a holder with bands or tapes which may be elastic; U.S. Pat. No. 2,292,030 issued to M. Kraft on Aug. 4, 1942; U.S. Pat. No. 2,577,398 which issued to V. Blake on Dec. 4, 1951; and U.S. Pat. No. 2,606,558 which issued to H. O. Kennette on Aug. 12, 1952 show liners secured with snap fasteners inside side-closing overpants; U.S. Pat. No. 4,022,210 which issued to Jacob A. Glassman on May 10, 1977 shows a liner secured to a diaper with spots of pressure sensitive adhesive. Additionally, U.S. Pat. No. 2,733,715 which issued to Y. L. Folk on Feb. 7, 1956 discloses Composite Training Pants and Diaper having unitized elasticized leg cuffs: leg cuffs wherein the longitudinal side edges of the training pants are joined to the longitudinal side edges of the diaper and jointly elasticized by elastic bands. Also, U.S. Pat. No. 4,597,760 which issued to Kenneth B. Buell on Jul. 1, 1986, discloses a waist-containment garment having a disposable elasticized insert. While these patents disclose a liner, diaper, and outer-garment configurations and combinations which have solved some of the problems associated with providing enough absorbent capacity for overnight requirements, they have not solved the problems associated with the absorbent article and liners being sold in separate packages. Having the absorbent article and liners sold only in separate packages is both costly and inconvenient to consumers.

Therefore, it is an object of the present invention to provide a package containing absorbent articles having a predetermined absorbent capacity, and at least one insert. When the insert is joined to the absorbent article, either before being placed in the package or by the caretaker before being placed on the wearer, the insert and the absorbent article together form a combined absorbent article having an absorbent capacity which is greater than the absorbent capacity of the absorbent article.

The above and other objectives of the present invention will be more readily apparent when considered in reference to the following description and when taken in conjunction with the accompanying drawings.

SUMMARY OF THE INVENTION

The present invention provides a package containing a plurality of absorbent articles and inserts. The package comprises at least one first absorbent article comprising a liquid pervious topsheet, a liquid impervious backsheet associated with the topsheet, and an absorbent core disposed between the topsheet and the backsheet. The first absorbent article has a predetermined absorbent capacity. The package also includes at least one insert having a liquid pervious topsheet, a liquid pervious backsheet associated with the topsheet, and an absorbent core disposed between the topsheet and the backsheet. The insert and the absorbent article may be placed in the package separately or one or more of the insets may be joined to an absorbent article before being placed in the package. When the insert and the absorbent article are joined together to form a combined absorbent article, the combined absorbent article has an absorbent capacity which is greater than the absorbent capacity of the first absorbent article. In a preferred embodiment, the first absorbent article comprises a disposable diaper.

BRIEF DESCRIPTION OF THE DRAWINGS

While the specification concludes with claims particularly pointing out and distinctly claiming the subject matter which is regarded as forming the present invention, it is believed that the present invention will be better understood from the following description which is taken in conjunction with the accompanying drawings in which like designations are used to designate substantially identical elements and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A preferred embodiment of an absorbent article is the disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, incontinent pads, training pants, and the like.

Figure 1:
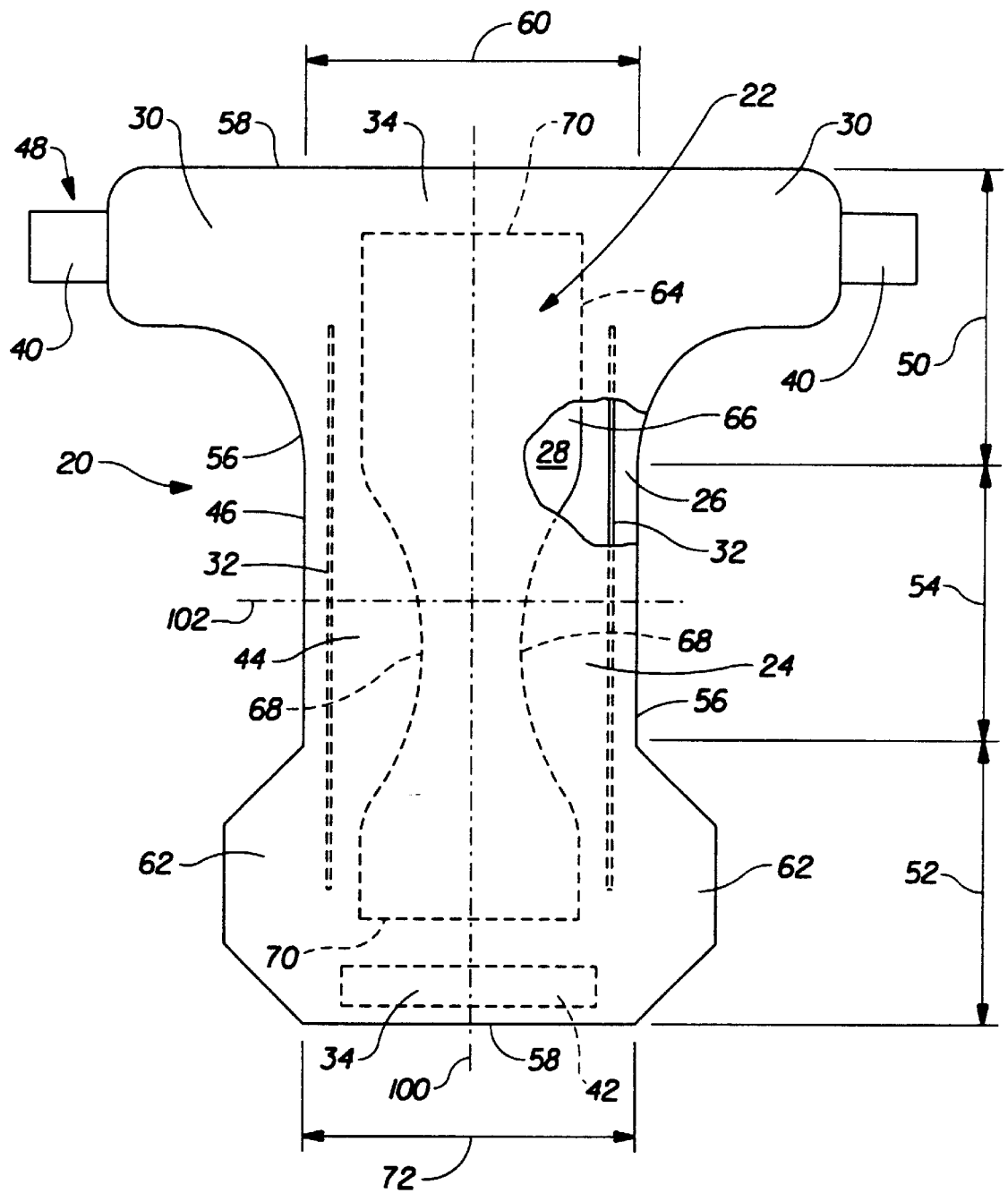
FIG. 1 is a plan view of a disposable diaper embodiment of the present invention having portions cut-away to reveal underlying structure, the inner surface of the diaper facing the viewer.

FIG. 1 is a plan view of the diaper 20 in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a containment assembly 22 comprising a liquid pervious topsheet 24; a liquid impervious backsheet 26 joined with the topsheet 24; and an absorbent core 28 positioned between the topsheet 24 and the backsheet 26. The diaper further comprises elasticized leg cuffs 32; ear flaps 62; elastic waist features 34; a fastening system 48 comprising a pair of first fastening members 40 and a second fastening member 42; and extensible side panels 30.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The diaper 20 is shown in FIG. 1 to have an inner surface 44 (facing the viewer in FIG. 1), an outer surface 46 opposed to the inner surface 44, a first waist region 50, a second waist region 52 opposed to the first waist region 50, a crotch region 54 positioned between the first waist region 50 and the second waist region 52, and a periphery which is defined by the outer perimeter or edges of the diaper 20 in which the longitudinal edges are designated 56 and the end edges are designated 58. The inner surface 44 of the diaper 20 comprises that portion of the diaper 20 which is positioned adjacent to the wearer's body during use (i.e., the inner surface 44 generally is formed by at least a portion of the topsheet 24 and other components joined to the topsheet 24). The outer surface 46 comprises that portion of the diaper 20 which is positioned away from the wearer's body (i.e., the outer surface 46 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The first waist region 50 and the second waist region 52 extend from the end edges 58 of the periphery to the crotch region 54. The first waist region 50 comprises a central region 60 and a pair of extensible side panels 30 which typically comprise the outer lateral portions of the first waist region 50. The second waist region 52 comprises a central region 72 and a pair of ear flaps 62 which typically comprise the outer lateral portions of the second waist region 52. The extensible side panels positioned in the first waist region 50 are designated 30 while the ear flaps in the second waist region 52 are designated 62.

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. Generally, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, preferred containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

The absorbent core 28 may be any absorbent member which is generally compressible, conformable, and non-irritating to the wearer's skin, and capable of absorbing and retaining liquids such as urine and other certain body exudates. As shown in FIG. 1, the absorbent core 28 has an outer surface 64, an inner surface 66, side edges 68, and waist edges 70. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or crosslinked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20. The size and absorbent capacity of the absorbent core 28 may also be varied to accommodate wearers ranging from infants through adults.

One embodiment of the diaper 20 has an asymmetric, modified T-shaped, absorbent core 28 having ears in the first waist region and a generally rectangular shape in the second waist region. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing acquisition/distribution zone of chemically stiffened fibers positioned over the absorbent storage cores as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 26 is positioned adjacent the outer surface 64 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. Further, the backsheet 26 may permit vapors to escape from the absorbent core 28 (i.e., breathable) while still preventing exudates from passing through the backsheet 26. Thus, the backsheet 26 may comprise a woven or nonwoven material, polymeric films such as thermoplastic films of polyethylene or polypropylene, or composite materials such as a film-coated nonwoven material. An example of a suitable backsheet is a thermoplastic film having a thickness of from about 0.012 mm (0.5 mil) to about 0.051 mm (2.0 mils). Other suitable materials for the backsheet 26 include RR8220 blown films and RR5475 cast films as manufactured by Tredegar Industries, Inc. of Terre Haute, Ind. The backsheet 26 is preferably embossed and/or matte finished to provide a more clothlike appearance. Another suitable backsheet is a laminate comprising a thermoplastic film secured to a nonwoven web of staple fibers.

The topsheet 24 is positioned adjacent the inner surface 66 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

There are a number of manufacturing techniques which may be used to manufacture the topsheet 24. For example, the topsheet 24 may be a nonwoven web of fibers. When the topsheet 24 comprises a nonwoven web, the web may be spunbonded, carded, wet-laid, melt-blown, hydroentangled, combinations of the above, or the like. A suitable topsheet 24 is carded and thermally bonded by means well known to those skilled in the fabrics art. A satisfactory topsheet 24 comprises staple length polypropylene fibers having a denier of about 2.2. As used herein, the term "staple length fibers" refers to those fibers having a length of at least about 15.9 mm (0.625 inches). Preferably, the topsheet 24 has a basis weight from about 18 to about 25 grams per square meter. A suitable topsheet is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. While each elasticized leg cuff 32 may be configured so as to be similar to any of the leg bands, side flaps, barrier cuffs, or elastic cuffs described above, each elasticized leg cuff 32 preferably comprises a gasketing cuff as described in the above-referenced U.S. Pat. No. 3,860,003.

The diaper 20 preferably further comprises an elastic waist feature 34 that helps provide improved fit and containment. The elastic waist feature 34 is that portion or zone of the diaper 20 which is intended to elastically expand and contract to dynamically fit the wearer's waist. The elastic waist feature 34 preferably extends longitudinally outwardly from at least one of the waist edges 70 of the absorbent core 28 and generally forms at least a portion of the end edge 58 of the diaper 20. Disposable diapers are generally constructed so as to have two elastic waist features, one positioned in the first waist region 50 and one positioned in the second waist region 52, although diapers can be constructed with a single elastic waist feature. Further, while the elastic waist feature 34 or any of its constituent elements can comprise a separate element affixed to the diaper 20, the elastic waist feature 34 may be constructed as an extension of other elements of the diaper such as the backsheet 26 or the topsheet 24, preferably both the backsheet 26 and the topsheet 24. The waist feature 34 may be constructed in a number of different configurations including those described in U.S. Pat. No. 4,515,595 issued to Kievit et al. on May 7, 1985 and the above referenced U.S. Pat. No. 5,151,092 issued to Buell; each of these references being incorporated herein by reference.

In a preferred embodiment of the present invention, the diaper 20 also comprises ear flaps 62 that extend laterally outwardly from each longitudinal edge 56 of the containment assembly 22 in the second waist region 52. The ear flaps 62 provide a structure to which the first waist region 50 can be attached to encircle the legs and waist of the wearer. The ear flaps 62 may take on a number of different sizes, shapes, configurations, and materials. The ear flaps 62 may comprise a portion of the material making up one or more of the diaper elements, including the topsheet 24, and the backsheet 26. Alternatively, the ear flaps 62 may comprise a separate element or a plurality of elements joined to the diaper. Suitable materials for use as the ear flaps 62 include woven webs; nonwoven webs; films, including polymeric films; foams; laminate materials including film laminates, nonwoven laminates, or zero strain laminates; elastomers; composites; or any combination of materials herein described or as described with respect to the extensible side panels as are known in the art. The ear flaps 62 may be joined to the containment assembly 22 by any means as known in the art; for example the ear flaps 62 may be continuously or intermittently bonded to the containment assembly using heated or unheated adhesive, heat bonding, pressure bonding, ultrasonic bonding, dynamic mechanical bonding or any other method that is known in the art.

The diaper 20 additionally comprises an extensible side panel 30 disposed adjacent each longitudinal edge 56 of the containment assembly 22 of the diaper 20, preferably in the first waist region 50. (As used herein, the term "disposed" means that an element(s) of the absorbent article is formed (joined and positioned) in a particular place or position as a unitary structure with other elements of the absorbent article or as a separate element joined to another element of the absorbent article.) The extensible side panels 30 provide an elastically extensible feature that provides a more comfortable and contouring fit by initially conformably fitting the diaper to the wearer and sustaining the fit throughout the time of wear well past when the diaper has been loaded with exudates since the extensible side panels 30 allow the sides of the diaper 20 to expand and contract. The extensible side panels 30 further provide more effective application of the diaper since even if the diaperer fits the diaper to the wearer asymmetrically, the diaper will "self-adjust" during wear to attain an improved fit. The extensible side panels 30 of the present invention also provide improved dynamic fit about the waist as well as the thigh of the wearer, reducing the possibility of sagging and gapping both at the waist and about the leg that can cause leakage, while increasing freedom of motion and wearer comfort in each area.

While the diaper 20 of the present invention preferably has extensible side panels 30 disposed in the first waist region 50; alternatively, the diaper 20 may be provided with extensible side panels 30 disposed in the second waist region 52 or in both the first waist region 50 and the second waist region 52. While the extensible side panels 30 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and U.S. patent application Ser. No. 08/155,048 entitled "Absorbent Article with Multi-Directional Extensible Side Panels", filed in the name of Miguel A. Robles, et al. on Nov. 19, 1993; each of which is incorporated herein by reference.

The diaper 20 is also preferably provided with a fastening system 48 for fitting the diaper on the wearer. The fastening system 48 maintains the first waist region 50 and the second waist region 52 in an overlapping configuration to form a side closure. The fastening system 48 further maintains tension in the extensible side panels 30 to hold the diaper 20 on the wearer as well as to provide for improved dynamic fit about the legs and waist of the wearer. The fastening system 48 may comprise any attachment means known in the art, including, but not limited to, pressure sensitive adhesives, cohesive materials, mechanical fastening means, such as hook and loop type fasteners, or any combination of these or any other attachment means as known in the art. Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987; each of which are incorporated herein by reference. Examples of other closure systems, including mechanical closure systems, useful in the present invention are disclosed in U.S. Pat. No. 4,869,724 issued to Scripps on Sep. 26, 1989; U.S. Pat. No. 4,848,815 issued to Scripps on Jul. 11, 1989; and U.S. Pat. No. 5,242,436 issued to Weil, Buell, Clear, and Falcone on Sep. 7, 1993; each of which are incorporated herein by reference.

The diaper 20 is preferably applied to a wearer by positioning one of the waist regions, preferably the first waist region 50, under the wearer's back and drawing the remainder of the diaper 20 between the wearer's legs so that the other waist region, preferably the second waist region 52, is positioned across the front of the wearer. The diaperer then wraps one extensible side panel 30 around the wearer, while grasping one of the first fastening members 40 disposed on each of the extensible side panels 30. The diaper then repeats this step for the other extensible side panel 30. The waist closure is formed by engagement of the first fastening members 40 to the second fastening member 42 located in the second waist region 52. With the formation of the waist closure, the diaper 20 is initially conformably fit about the wearer. If the diaper 20 has been fitted asymmetrically, the diaper 20 will self-adjust during wear to attain an improved fit. Once fitted to the wearer, the extensible side panels 30 expand and contract in conjunction with the motions of the wearer to provide improved dynamic fit throughout the time of wear, well past when the diaper 20 has been loaded with exudates. This improved dynamic fit reduces sagging and gapping of the diaper 20 in the waist and thigh regions while increasing wearer comfort.

Figure 2:
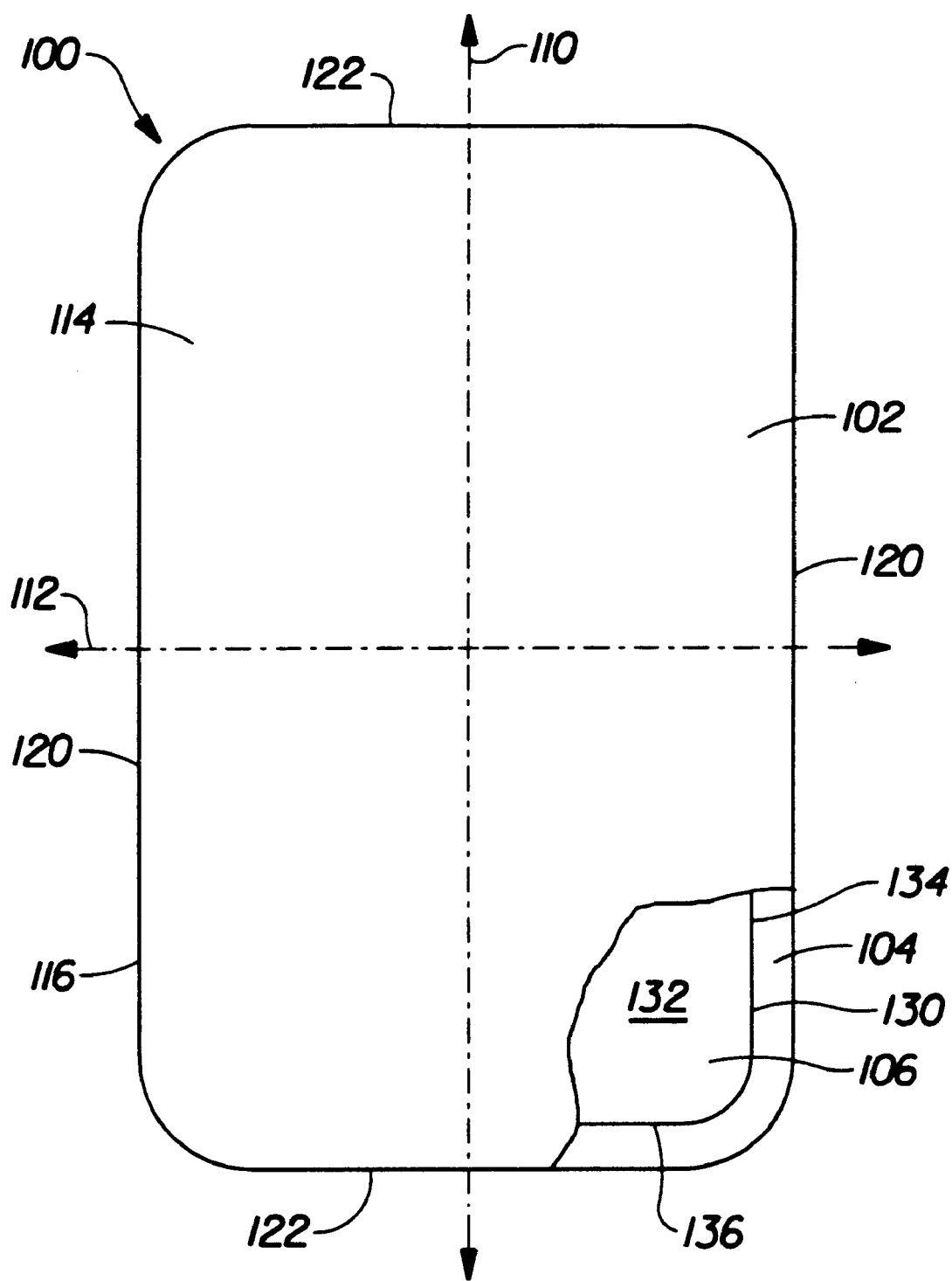
FIG. 2 is a plan view of an insert embodiment of the present invention having portions cut-away to reveal underlying structure, the inner surface of the insert facing the viewer.

FIG. 2 is a plan view of a preferred embodiment of an insert 100 in its flat-out state with portions of the structure being cut-away to more clearly show the construction of the insert 100 and with the portion of the insert 100 which faces or contacts the wearer, the inner surface, oriented towards the viewer. As shown in FIG. 2, the insert 100 preferably comprises a liquid pervious topsheet 102; a liquid pervious backsheet 104 joined with the topsheet 102; and an absorbent core 106 positioned between the topsheet 102 and the backsheet 104.

The insert 100 also has two centerlines, a longitudinal centerline 110 and a transverse centerline 112. The insert 110 has an inner surface 114 (facing the viewer in FIG. 2), an outer surface 116 opposed to the inner surface 114, and a periphery which is defined by the outer perimeter or edges of the insert 100 in which the longitudinal edges are designated 120 and the end edges are designated 122. The inner surface 114 of the insert 100 comprises that portion of the insert which is positioned adjacent to the wearers body during use (i.e., the inner surface 114 is generally is formed by at least a portion of the topsheet 102 and other components joined to the topsheet 102). The outer surface 116 comprises that portion of the insert 100 which is positioned away from the wearer's body (i.e., the outer surface 116 is generally formed by at least a portion of the backsheet 104 and other components joined to the backsheet 104).

FIG. 2 shows a preferred embodiment of the insert 100 in which the topsheet 102 and the backsheet 104 have length and width dimensions generally larger than those of the absorbent core 106. The topsheet 102 and the backsheet 104 extend beyond the edges of the absorbent core 106 to thereby form the periphery of the insert 100.

The absorbent core 106 may be any absorbent member which is generally compressible, conformable, and non-irritating to the wearer's skin, and capable of absorbing and retaining liquids such as urine and other certain body exudates. As shown in FIG. 2, the absorbent core 106 has an outer surface 130, an inner surface 132, side edges 134, and end edges 136. The absorbent core 106 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 106 may vary (e.g., the absorbent core may have varying caliper zones, a hydrophilic gradient, a superabsorbent gradient, or lower average density and lower average basis weight acquisition zones; or may comprise one or more layers or structures). However, the total absorbent capacity of the absorbent core 106 should be compatible with the design loading and the intended use of the insert 100. The size and absorbent capacity of the absorbent core 106 may also be varied to accommodate wearers ranging from infants through adults.

Exemplary absorbent structures for use as the absorbent core 106 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing acquisition/distribution core of chemically stiffened fibers positioned over the absorbent storage cores as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 104 is positioned adjacent the outer surface 130 of the absorbent core 106 and is preferably joined thereto by attachment means (not shown) such as those well known in the art. For example, the backsheet 104 may be secured to the absorbent core 106 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 104 is pervious to liquids (e.g., urine), allowing exudates absorbed and contained in the absorbent core 106 to flow from insert 100 into disposable diaper 20. The backsheet 106 is preferably compliant, soft feeling and non-irritating to the wearer's skin. A suitable backsheet 106 may be manufactured from a wide range of materials, such as those used to manufacture the liquid pervious topsheet 102 as described in greater detail below.

The topsheet 102 is positioned adjacent the inner surface 132 of the absorbent core 106 and is preferably joined thereto and to the backsheet 104 by attachment means (not shown) such as those well known in the art. Suitable attachment means are described with respect to joining the backsheet 104 to the absorbent core 106. In a preferred embodiment of the present invention, the topsheet 102 and the backsheet 104 are joined directly to each other in the insert periphery and are indirectly joined together by directly joining them to the absorbent core 106 by the attachment means (not shown).

The topsheet 102 is compliant, soft feeling, and non-irritating to the wearer's skin. Further, the topsheet 102 is preferably liquid pervious permitting liquids (e.g., urine) to readily penetrate through its thickness. A suitable topsheet 102 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 102 is preferably made of a hydrophobic material to isolate the wearer's skin from liquids which have passed through the topsheet 102 and are contained in the absorbent core 106 (i.e. to prevent rewet). If the topsheet 102 is made of a hydrophobic material, at least the upper surface of the topsheet 102 is treated to be hydrophilic so that liquids will transfer through the topsheet more rapidly. This diminishes the likelihood that body exudates will flow off the topsheet 102 rather than being drawn through the topsheet 102 and being absorbed by the absorbent core 106. The topsheet 102 can be rendered hydrophilic by treating it with a surfactant. Suitable methods for treating the topsheet 102 with a surfactant include spraying the topsheet 102 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

There are a number of manufacturing techniques which may be used to manufacture the topsheet 102. For example, the topsheet 102 may be a nonwoven web of fibers. When the topsheet 102 comprises a nonwoven web, the web may be spunbonded, carded, wet-laid, melt-blown, hydroentangled, combinations of the above, or the like. A suitable topsheet 102 is carded and thermally bonded by means well known to those skilled in the fabrics art. A satisfactory topsheet 102 comprises staple length polypropylene fibers having a denier of about 2.2. As used herein, the term "staple length fibers" refers to those fibers having a length of at least about 15.9 mm (0.625 inches). Preferably, the topsheet 102 has a basis weight from about 18 to about 25 grams per square meter. A suitable topsheet is manufactured by Veratec, Inc., a Division of International Paper Company, of Walpole, Mass. under the designation P-8.

Figure 3:
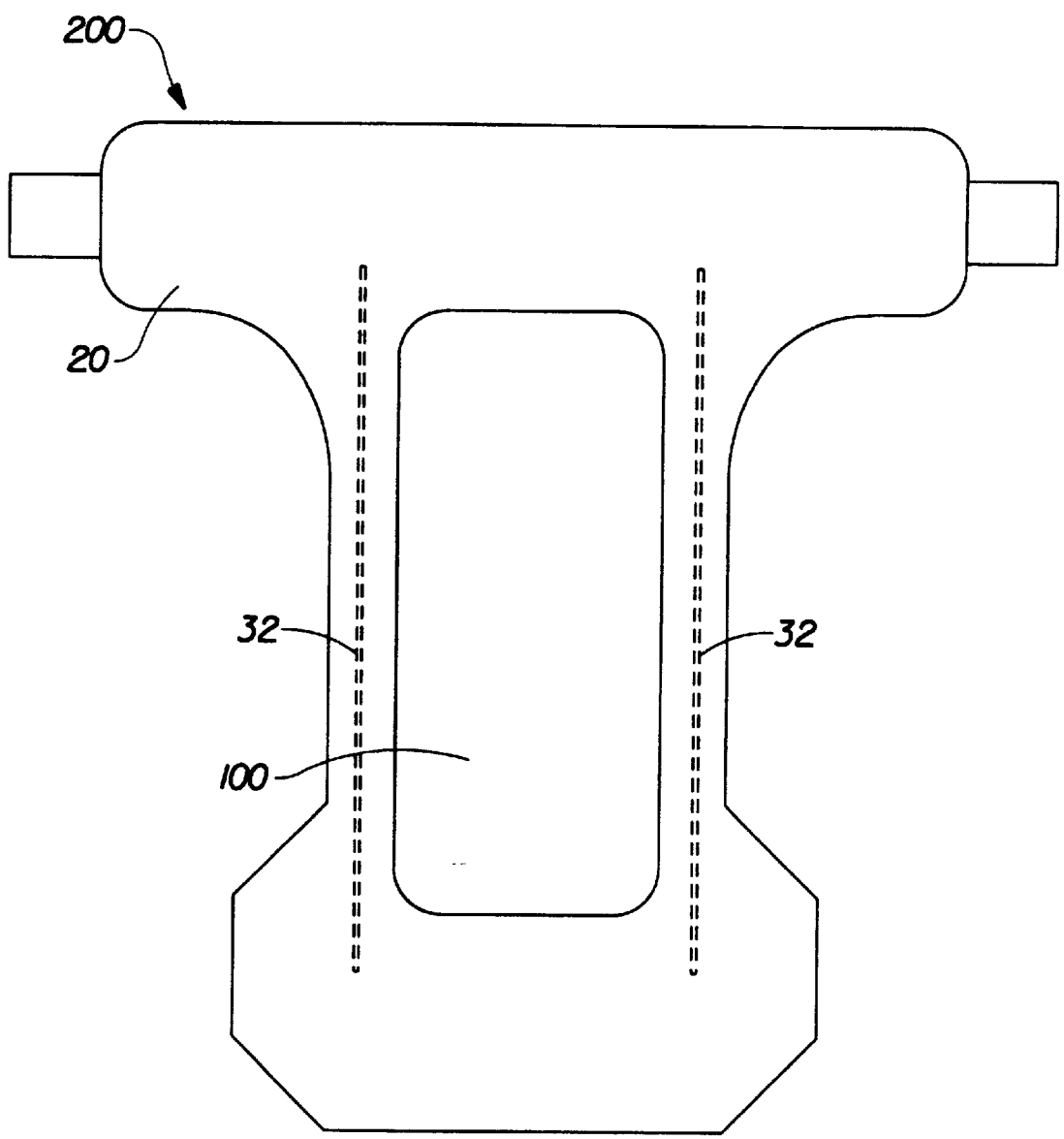
FIG. 3 is a plan view of a combined disposable diaper of the present invention.

FIG. 3 is a plan view of a combined disposable diaper 200 in its flat-out condition. The combined disposable diaper 200 comprises a disposable diaper 20 and an insert 100. The insert 100 may be joined to the disposable diaper 20 to form the combined disposable diaper 200 before being placed in the package, or by the caretaker or the wearer before being placed on the wearer. As can be seen in FIG. 3, the insert 100 has overall length and width dimensions somewhat less than that of disposable diaper 20. Preferably, the insert 100 has width dimensions such that insert 100 will fit between opposing elasticized leg cuffs 32. In addition, it is preferable that the insert 100 have an overall plan-view size which is less than the plan-view size of the absorbent core 28 of the disposable diaper 20.

Insert 100 may be secured to disposable diaper 20 by means well known in the art. Such as adhesives, buttons, mechanical fasteners, snaps, hook and loop type fasteners, etc. Whatever fastening means is selected, it is preferable to select a fastening means for securing the insert 100 to the diaper 20 such that the backsheet portion 104 of insert 100 remains fluid pervious allowing fluids absorbed and contained within the insert 100 to flow from insert 100 into disposable diaper 20.

A preferred method for treating incontinent infirmities in infants and other incontinent individuals is to use a disposable diaper having a predetermined absorbent capacity on the individual during periods when relatively low quantities of bodily fluids are expected to be discharged by the individual, such as during daytime use. A combined disposable diaper comprising a diaper and an insert, which has a greater absorbent capacity than the absorbent capacity of a single disposable diaper is placed on the individual during periods when relatively high quantities of bodily fluids are expected to be discharged by the individual, such as during overnight use.

Preferably, the absorbent capacity of the combined diaper is at least about 20% greater than the absorbent capacity of a single diaper, more preferably at least about 50% greater, and most preferably at least about 75% greater. In a particularly preferred embodiment of the present invention, the absorbent capacity of a combined diaper is at least about 100% greater than the absorbent capacity of a single diaper.

For convenience and ease of application by the consumer, a plurality of disposable diapers and inserts are packaged in the same package. The ratio of the number of diapers to inserts packaged in a single package ranges from about 1:1 to about 10:1. Preferably, the ratio of the number of diapers to inserts is greater than 1:1 to about 10:1. More preferably, the ratio of diapers to inserts is about 5:1, even more preferably about 4:1, and most preferably about 3:1. Thus, the inserts may be used in combination with disposable diapers during periods when relatively high quantities of bodily fluids are expected to be discharged by the wearer, such as during overnight use, and the remaining disposable diapers may be used without the inserts during periods when relatively low quantities of bodily fluids are expected to be discharged by the wearer, such as during daytime use.

The package may also include a plurality of absorbent articles or inserts that have different absorbent capacities in order to provide an even greater variety of absorbent capacities. For example, the package may include one or more absorbent articles having a first absorbent capacity, one or more absorbent articles having a second absorbent capacity and one or more inserts that may be used in combination with either the first or the second absorbent articles. In this example, the package would provide combinations that allow up to four different absorbent capacities: the first absorbent article, the second absorbent article, the first absorbent article with an insert and the second absorbent article with an insert. In addition, three or more absorbent articles having different absorbent capacities may be provided. Multiple inserts having different absorbent capacities may also be packaged with one or more absorbent articles to provide combinations that allow different absorbent capacities. Multiple inserts may also be used in combination with one absorbent article to allow for different absorbent capacities.

Figure 4:
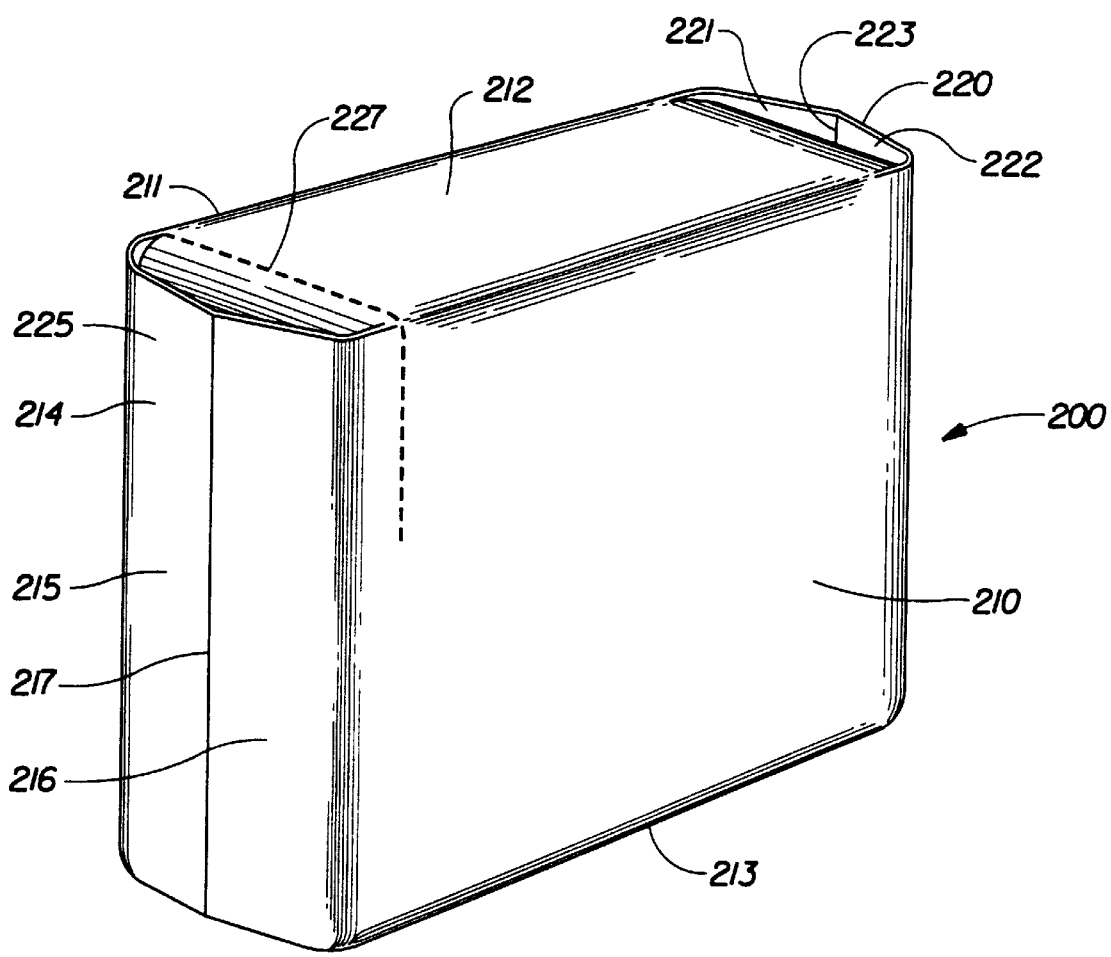
FIG. 4 is a simplified perspective view of a package containing compressed diapers and inserts.

Referring now to FIG. 4, package 200 generally has the shape of a parallelepiped and represents a filled bag containing compressed diapers 20 and compressed inserts 100. Package 200 comprises a front panel 210, a back panel 211, a top panel 212, a bottom panel 213, and side panels 214 and 220. The side panel 214 comprises two sections 215 and 216 that are secured to one another along joinder line 217. The side panel 220 comprises two sections 221 and 222 that are secured to one another along joinder line 223. An opening device 225 is preferably provided in side panel 214. Opening device 225 preferably comprises a line of weakness 227. Line of weakness preferably extends through a portion of the front panel 210, the top panel 212 and into a portion of the back panel 211.

Package 200 may be made of paper, or any recyclable material and laminate structures comprised of two or more of the aforementioned materials. In addition, package 200 may also be made of nonbiodegradable or nonrecyclable materials, such as polymeric films that employ the same structure of the described package.

Other structures for use as the package 200 of the present invention are described in U.S. Pat. No. 4,846,587 issued to Hull on Jul. 11, 1989; U.S. Pat. No. 4,934,535 issued to Muckenfuhs, et al. on Jun. 19, 1990; U.S. Pat. No. 4,966,286 issued to Muchenfuhs on Oct. 30, 1990; U.S. Pat. No. 5,036,978 issued to Frank, et al. on Aug. 6, 1991; U.S. Pat. No. 5,050,742 issued to Muckenfuhs on Sep. 24, 1991; and U.S. Pat. No. 5,054,619 issued to Muckenfuhs on Oct. 8, 1991; each of which is incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package comprising:
   (a) a front panel and a back panel connected to one another by a top panel, a bottom panel and a pair of side panels;
   (b) a plurality of first absorbent articles comprising a liquid pervious first topsheet, a liquid impervious first backsheet joined to said first topsheet, and a first absorbent core disposed between said first topsheet and said first backsheet, said first absorbent article having a first predetermined absorbent capacity; and (
   c) at least one insert adapted to be joined to one of said first absorbent articles to form a combined absorbent article, said insert comprising a liquid pervious second topsheet, a liquid pervious second backsheet joined to said second topsheet, and a second absorbent core disposed between said second topsheet and said second backsheet;
   wherein said package includes a greater number of said first absorbent articles than said inserts.

2. The package of claim 1, wherein said first absorbent articles are disposable diapers.

3. The package of claim 1, wherein said first absorbent core has a first length and a first width, said insert having a second length and a second width, said second length of said insert being less that said first length of said first absorbent core and said second width of said insert being less than said first width of said first absorbent core.

4. The package of claim 1, wherein said insert is joined to one of said first absorbent articles forming said combined absorbent article.

5. The package of claim 1, wherein said insert comprises a means for fastening said insert to one of said first absorbent articles.

6. The package of claim 1, wherein said package includes a first number of said first absorbent articles and a second number of said at least one insert, said package further including a ratio of said first number to said second number ranging from greater than 1:1 to about 10:1.

7. The package of claim 6, wherein the ratio of said first number to said second number is about 5:1.

8. The package of claim 6, wherein the ratio of said first number to said second number is about 4:1.

9. The package of claim 6, wherein the ratio of said first number to said second number is about 3:1.

10. The package of claim 1, wherein said combined absorbent article has an absorbent capacity greater than said first predetermined absorbent capacity of said first absorbent article.

11. The package of claim 10, wherein said absorbent capacity of said combined absorbent article is at least about 20% greater than said first predetermined absorbent capacity of said first absorbent article.

12. The package of claim 10, wherein said absorbent capacity of said combined absorbent article is at least about 50% greater than said first predetermined absorbent capacity of said first absorbent article.

13. The package of claim 10, wherein said absorbent capacity of said combined absorbent article is at least about 100% greater than said first predetermined absorbent capacity of said first absorbent article.

14. The package of claim 1 further comprising at least one second absorbent article, said second absorbent article comprising a liquid pervious third topsheet, a liquid impervious third backsheet joined to said third topsheet, and a third absorbent core disposed between said third topsheet and said third backsheet, wherein said package includes a greater number of said first and said second absorbent articles than said inserts.

15. The package of claim 14, wherein said second absorbent article has a second predetermined absorbent capacity that is different than said first predetermined quantity of said first absorbent article.

16. The package of claim 14, wherein said insert is adapted to be joined to one of said second absorbent articles.

17. A method of treating incontinent infirmities of a wearer comprising:
   (a) providing a package of absorbent articles including:
      (i) a plurality of first absorbent articles comprising a liquid pervious first topsheet, a liquid impervious first backsheet joined to said first topsheet, and a first absorbent core disposed between said first topsheet and said first backsheet, said first absorbent article having a predetermined absorbent capacity; and
      (ii) at least one insert adapted to be joined to one of said first absorbent articles to form a combined absorbent article, said insert comprising a liquid pervious second topsheet, a liquid pervious second backsheet joined to said second topsheet, and a second absorbent core disposed between said second topsheet and said second backsheet, wherein said package includes a greater number of said first absorbent articles than said inserts;

(b) using said absorbent article having said predetermined absorbent capacity on the wearer during a first period having a first expected quantity of bodily fluid discharge; and (c) using said combined absorbent article having an absorbent capacity greater than said predetermined absorbent capacity on the wearer during a second period having a second expected quantity of bodily fluid discharge, said second expected quantity being greater than said first expected quantity.

* * * * *